(12) United States Patent
Lin et al.

(10) Patent No.: US 6,842,670 B2
(45) Date of Patent: Jan. 11, 2005

(54) EYE-TRACKING DRIVING SYSTEM

(75) Inventors: Chern-Sheng Lin, Taichung (TW);
Mau-Shiun Yeh, Chia-Yi (TW); Wen Chen Chen, Pa-Te (TW); Chao Ning Chan, Chu-Pei (TW); Tzung-Hang Wu, Kaohsiung Hsien (TW); Hui-Fen Chiang, Chung-Li (TW)

(73) Assignee: Chung Shan Institute of Science and Technology, Tao-Yuan Hsien (TW)

( * ) Notice: Subject to any disclaimer, the term of this patent is extended or adjusted under 35 U.S.C. 154(b) by 88 days.

(21) Appl. No.: 10/428,086

(22) Filed: May 2, 2003

(65) Prior Publication Data

US 2004/0220704 A1 Nov. 4, 2004

(51) Int. Cl.[7] .............................. A61B 3/10; A61B 3/14; A61B 5/103
(52) U.S. Cl. ............................. 701/1; 702/127; 345/629
(58) Field of Search .............................. 701/1; 702/127, 702/150; 345/7, 8, 629; 359/630; 382/100, 276, 293; 340/556, 573.1; 396/51

(56) References Cited

U.S. PATENT DOCUMENTS

| | | | | |
|---|---|---|---|---|
| 3,712,716 A | * | 1/1973 | Cornsweet et al. | ......... 351/210 |
| 5,410,376 A | * | 4/1995 | Cornsweet et al. | ......... 351/210 |
| 5,802,220 A | * | 9/1998 | Black et al. | ................ 382/276 |
| 5,926,251 A | * | 7/1999 | Okumura | .................... 351/209 |
| 6,401,050 B1 | * | 6/2002 | Cooke et al. | ............... 702/127 |
| 6,637,883 B1 | * | 10/2003 | Tengshe et al. | ............. 351/210 |

* cited by examiner

Primary Examiner—Tan Q. Nguyen
Assistant Examiner—Dalena Tran
(74) Attorney, Agent, or Firm—Rosenberg, Klein & Lee

(57) ABSTRACT

This invention relates to an eye-tracking driving system, especially to an eye-tracking system controlled by the user's eye. It not only utilizes the unique eye-controlled method, but also avoids contacting with the user's eyes or skin. It is suitable for the disabled persons or the elderly so that they can drive a powered vehicle easily. The system mainly includes a display device, an eye-tracking device, a calculating device, a controller and a powered vehicle. This system can effectively capture the image around the user's eye and then precisely determine the pupil center. Based on the position of the pupil center, the power vehicle can be controlled.

11 Claims, 8 Drawing Sheets

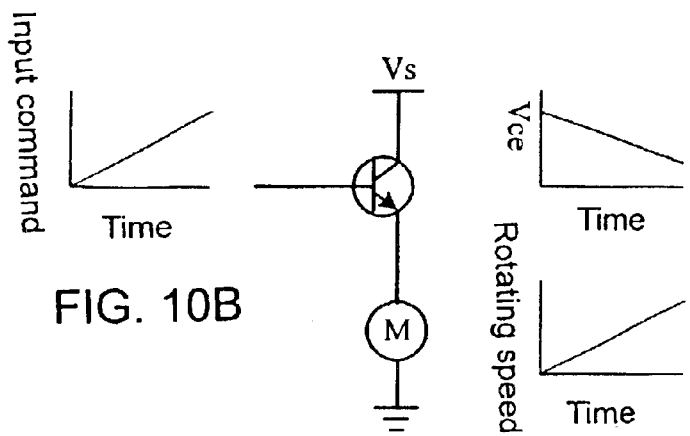
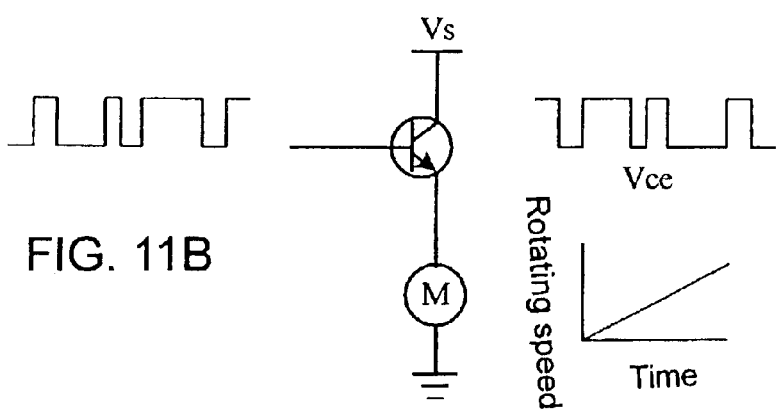
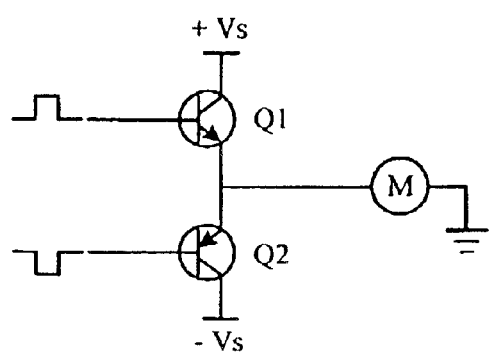
FIG. 12

EYE-TRACKING DRIVING SYSTEM

BACKGROUND OF INVENTION

1. Field of the Invention

The present invention relates to an eye-tracking driving system, especially to an eye-tracking system controlled by the user's eye. It not only utilizes the unique eye-controlled method, but also will not contact the user's eyes or skin. It is suitable for the disabled persons or the elderly so that they can drive a powered vehicle easily.

2. Description of the Prior Art

Due to the rapid development of medical technology, the life of a human is significantly prolonged. The death rate decreases. The averaged age of whole society gradually moves up. Accordingly, many problems such as medical care for disabled persons and the elderly occur. In Taiwan, the elderly was over 7% of the population in 1994. In September of 2000 the elderly (age above 65) became 1.9 million which is 8.6% of the total population. In addition, the registered physical disabled and mental diseased persons in the end of 2000 were 711,064 persons. In which, 306,169 persons are the physical disabled persons. For those persons (disabled persons and the elderly), they can not walk or run like a normal person. So, the powered wheelchair or the mini electric tricycle will be the most reliable auxiliary equipment for transportation.

A general powered wheelchair is controlled by a joystick-like device. Except the joystick-like input device, there are at least two other methods to control, such as the head-gesture control and mouth-blowing control. However, for some seriously disabled persons, all these devices mentioned above are not suitable. So, the eye control (or eye-tracking control) might be the last available choice.

With regard to the eye-tracking research, it can be traced back to the nineteen century. However, all the existing eye-tracking methods can be classified into the following three types.

(1) The Limbus tracking method. Basically, it utilizes a light projects into the eyeball and then reflect from the eyeball. And, it has a video camera to capture the image around the eyeball. By analyzing the variation of the reflected light from the eyeball to determine the moving direction of the eyeball. The disadvantage of this method is that the upper boundary and the lower boundary of the eyeball often block by the upper eyelid and lower eyelid respectively. In addition, its resolution is very low. Plus, its initial calibration procedure is quite lengthy (to check nine points shown on the screen three times). Besides, the distance between the head and the video camera must be remained fixed. Thus, it is impossible to use it for long time.

The electro-oculography (EOG) method. The researcher attaches several electricity sensors (or electrodes) around the skin of the eye. This electro-oculography (EOG) technology detects eye movements from the electrical measurement of the difference in potential between the cornea and the retina. Essentially, eye movements are accompanied by the appearance of electric signals. In the front of the head, the corneal to potential creates an electric field, which changes in orientation as the eyeball rotates. Electrodes placed around the eye can detect these electrical signals. For example, when the eye moves to the right, a positive voltage difference is measured. If the eye moves to the left, another negative voltage difference is measured. Hence, it can determine the eye's moving direction. However, sweat might affect the electrical signal read out. So the signals become unstable and unreliable. In addition, the electrodes are adhered on the skin of the user, so it limits its practical application.

(3) The coil search method. A tiny coil is sandwiched by a pair of contact lens. A magnetic field is created around the eyeball. Once the eyeball rotates, the movement of the contact lens with the coil can be observed after signal processing. But, it is not suitable for wearing such contact lens too long. This kind of contact lens might injure the user.

Therefore, it is desired to develop a new powered vehicle that is controlled by a new eye-tracking system.

SUMMARY OF THE INVENTION

The primary object of the present invention is to provide an eye-tracking driving system. It utilizes a unique eye-control method to drive a powered wheelchair or vehicle. This system will not cause contact injury and discomfort to the user.

Another object of the present invention is to provide an eye-tracking driving system. It will satisfy the basic need of a disabled person for driving a powered vehicle by oneself.

In order to achieve above objects and solve the existing problems, the present invention is provides an eye-tracking driving system. It comprises:

a display device disposed in front of a user to look at;

an eye-tracking device having a fixing band portion and a transparent goggles portion, the transparent goggles portion having a video capturing device for obtaining a human pupil area image and an auxiliary light for providing enough brightness of the human pupil area image;

a calculating device to input the human pupil area image via an image capturing interface card and then to calculate a center point of a pupil of the human pupil area image that is defined as a pupil center and to determine staying times and staying positions of the pupil center, and finally to output one of corresponding operation commands, the operation commands at least including: a left turn command, a right turn command, a forward command, a reverse command, and a stop command; wherein the human pupil area image is divided into nine zones substantially consisting by three columns and three rows so as to form a upper left zone, a top zone, a upper right zone, a left zone, a central zone, a right zone, a lower left zone, a bottom zone, and a lower right zone, the central zone, upper left zone, upper right zone, lower left zone, lower right zone are corresponding to the stop command, the left zone, right zone, top zone, and bottom zone are corresponding to the left turn command, right turn command, forward command and reverse command respectively;

a controller to convert the operation command that is an output from the calculating device into a left wheel driving command and a left wheel driving command;

a powered vehicle including a seat, a left driving system, a left wheel, a right driving system, and a right wheel, wherein the left wheel driving system can drive the left wheel according to the left driving command, and the right wheel driving system can drive the right wheel according to the right driving command.

BRIEF DESCRIPTION OF THE DRAWINGS

FIG. 10A shows the electric circuit of a general linear driving device;

FIG. 10B shows the input voltage of the circuit in FIG. 10A;

FIG. 10C shows the output voltage (Vce) of the circuit in FIG. 10A;

FIG. 10D shows revolution speed of the output of the motor in FIG. 10A;

FIG. 11A is a circuit diagram of the switching speeder;

FIG. 11B shows the input voltage of the circuit in FIG. 11A;

FIG. 11C shows its output voltage (Vce) of the circuit in FIG. 11A;

FIG. 11D shows the output of the motor in FIG. 11A;

FIG. 12 is a push-pull typed circuit;

DETAILED DESCRIPTION OF THIS INVENTION

Figure 1:
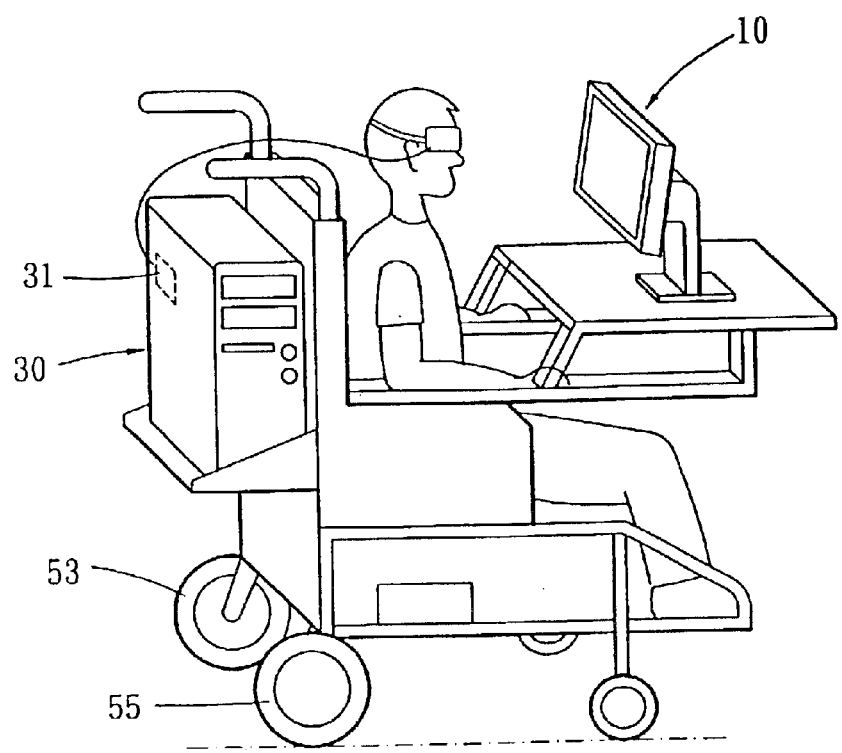
FIG. 1 is a perspective view of the present invention.

As shown in FIGS. 1 to 8, this invention relates to an eye-tracking driving system. An eye-tracking driving wheelchair is used as an example of the first embodiment of this invention. It mainly comprises a display device 10, an eye-tracking device 20, a calculating device 30, a controller 40 and a powered vehicle 50.

Referring to FIG. 1, this display device 10 is disposed in front of a user to look at. Usually, it can be a computer screen or a mini screen within a pair of goggles fitted on the user's head. In this embodiment, a 15-inch LCD (liquid crystal display) screen is used. A left turn mark, a right turn mark, a forward mark and a reverse mark are disposed on a left, right, upper, and lower positions of the screen. Similarly, there are four stop marks (not shown) disposed on four corners of the screen. In addition, the screen also shows the image in front of the user so that the user can control this invention easily. Or, display device 10 can be a foldable structure (not shown) so that it can be folded up or down depending on the user's need.

Figure 2:
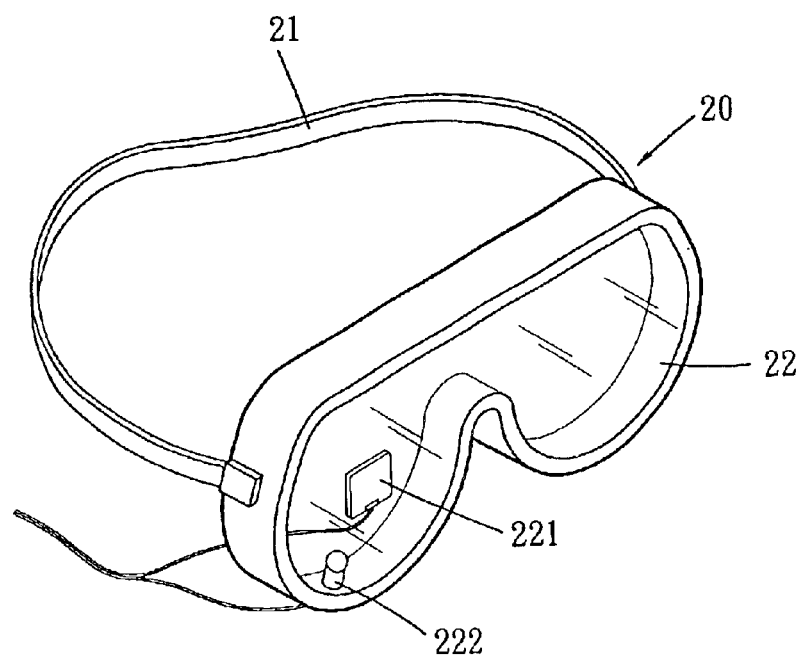
FIG. 2 is a perspective view of the eye-tracking device of this invention.
Figure 3:
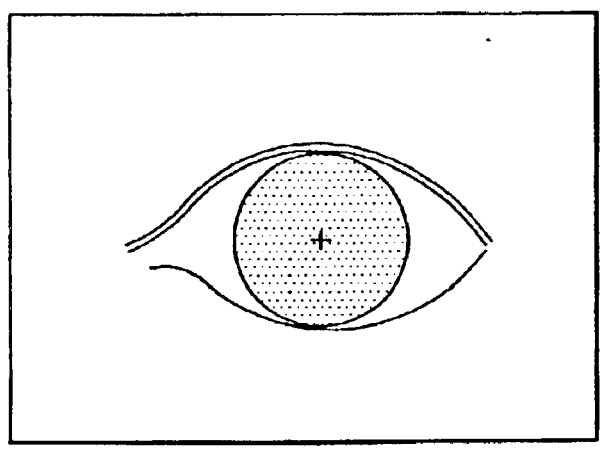
FIG. 3 illustrates a human pupil area image.
Figure 4:
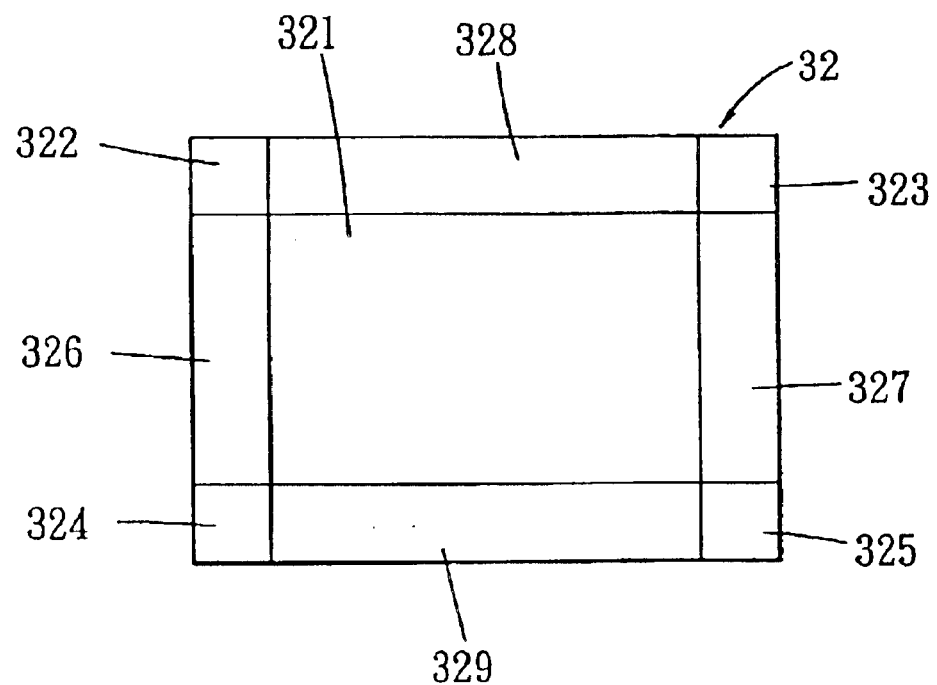
FIG. 4 is a illustration for the divided nine zones.
Figure 5:
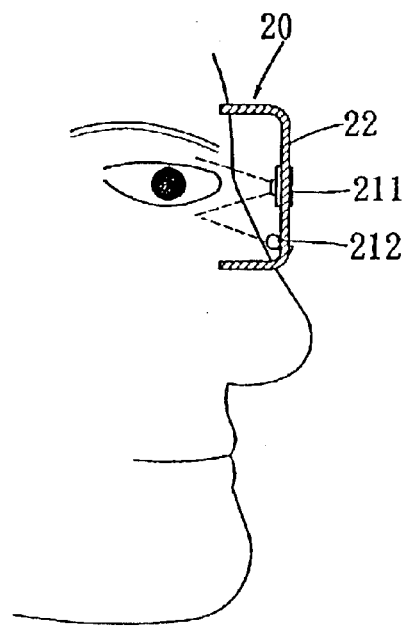
FIG. 5 is a cross-sectional view of the display device.

As illustrated in FIG. 2, the eye-tracking device 20 can be mounted on the user's head and has a fixing band portion 21 and a transparent goggles portion 22. The transparent goggle portion 22 has a video capturing device 221 for obtaining a human pupil area image and an auxiliary light 222 for providing enough brightness of the human pupil area image as shown in FIG. 3. Furthermore, referring to FIG. 5, the video capturing device 221 can be a pinhole mini camera that has a base board. Practically, if this type of camera can capture a roughly 500×500 pixels resolution, it will be good enough for later image processing. The auxiliary light 222 is disposed at a predetermined position beneath the video capturing device 221. A low-wattage electric light bulb (such as 5 Watts) is used in order to cause any comfortless feeling for the user's eyes.

With regard to the calculating device 30, as illustrated in FIG. 1 it can be a personal computer (or a notebook computer) to input the human pupil area image obtained by the video capturing device 221 via an image capturing interface card 31. Then, it will calculate a center point of a pupil of the human pupil area image that is defined as a pupil center and then to determine staying times and staying positions of said pupil center, and finally to output one of corresponding operation commands. The operation commands at least includes a left turn command, a right turn command, a forward command, a reverse command, and a stop command. This human pupil area image is divided into nine zones 32 substantially consisting by three columns and three rows so as to form a upper left zone 322, a top zone 328, a upper right zone 322, a left zone 326, a central zone 321, a right zone 327, a lower left zone 324, a bottom zone 329, and a lower right zone 325. Within the nine zones 32, the central zone 321, upper left zone 322, upper right zone 323, lower left zone 324, lower right zone 325 are corresponding to the stop command. The left zone 326, right zone 327, top zone 328, and bottom zone 329 are corresponding to the left turn command, right turn command, forward command and reverse command respectively. Practically, when the pupil center falls into one specific zone of the nine divided zones and lasts for a period of time, the user's command is obtained. This can be briefly called the nine-zone method. However, because the video capturing device 221 is disposed beneath the user's eye (not in front of the user's eye), when the eye move horizontally, the captured moving path of the pupil center is a curve (not a straight line). Therefore, the calculating device 30 must proceed another coordinate system conversion via a calibration processing. All the details about this calibration processing will be discussed later.

Figure 6:
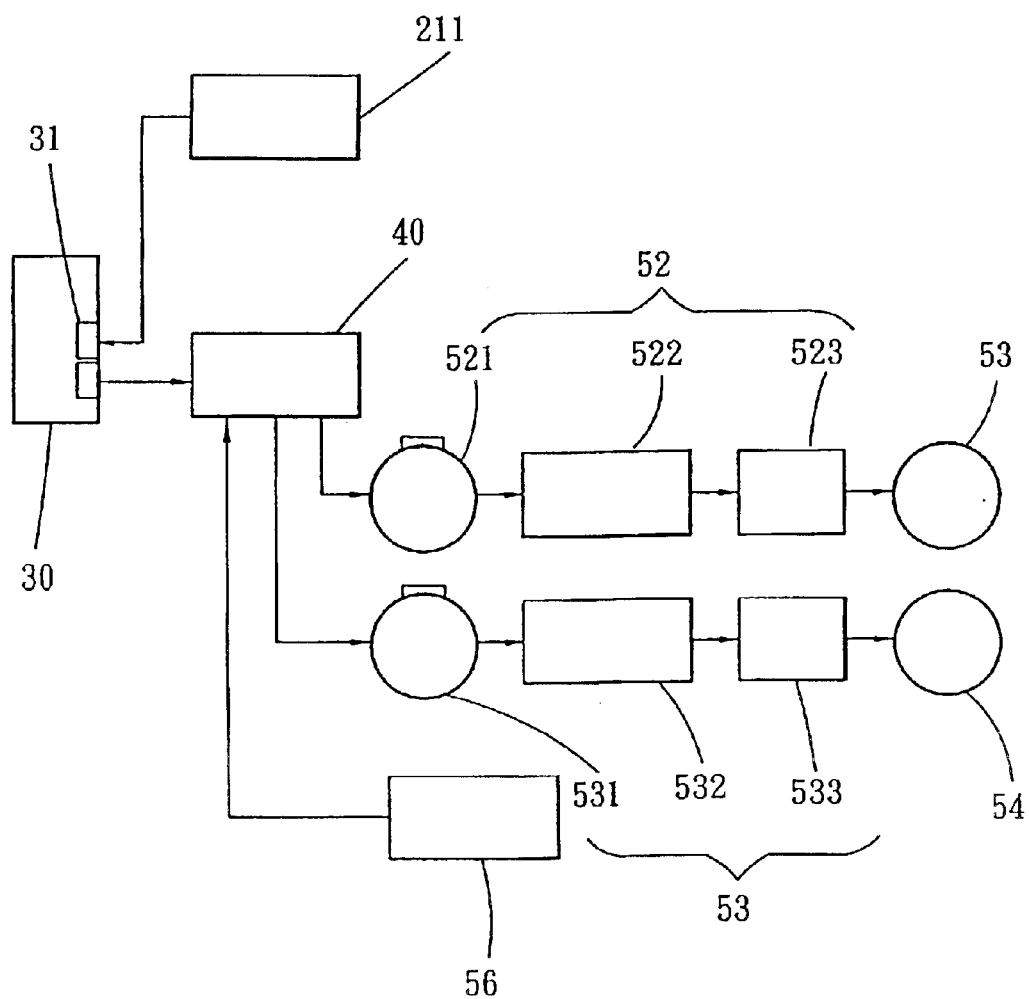
FIG. 6 shows the whole system of this invention.
Figure 7:
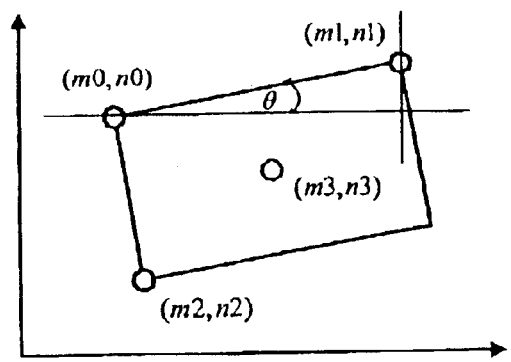
FIG. 7 shows four reference points for calibration.

Referring to FIG. 6, the controller 40 is able to convert the operation command that is an output from the calculating device 30 into a left wheel driving command and a left wheel driving command.

About the powered vehicle 50, it includes a seat 51 (as shown in FIG. 1), a left driving system 52, a left wheel 53, a right driving system 54, and a right wheel 55 (all as shown in FIG. 6). Of course, it usually includes a battery 56. In this embodiment, the left wheel driving system 52 can drive said left wheel 53 according to the left driving command. The right wheel driving system 54 can drive the right wheel 55 according to the right driving command. Moreover, the left driving system 52 further comprises a left motor 521, a left gear box 522 and a left clutch 523. The right driving system 54 further comprises a right motor 541, a right gear box 542 and a right clutch 543.

In this embodiment, the powered vehicle 50 is a powered wheelchair. The wheelchair is driven by a pair of motors (namely the left motor 521 and the right motor 541). The controller 40 can control these two motors 521, 541. In order to make a left turn or a right turn, the rotation speeds of the left wheel and the right wheel must be different. Also, it must combine with the existing forward or reverse command together. The speed control of these two motors can be achieved by an existing commonly used P-I (proportion-integration) control technique as compensation. About this P-I control technique, because it is a prior art, its detailed description is omitted.

With regard to the actual operation of this invention, the user sits on the seat 51 of the powered vehicle 50 and the eye-tracking device 20 is mounted on the user's head. Hence, the eye-tracking device 20 can obtain the human pupil area images continuously. The image dada will be processed by the calculating device 30 and find out the instant position of the pupil center. Also, by means of determining the staying time and staying position, it can be converted into the corresponding operation command. The operation commands at least include a left turn command, a right turn command, a forward command, a reverse command, and a stop command. For example, if the user wants to turn right, the user's eyes just move to the right so that this powered vehicle 50 can be controlled by the user's eyes.

Concerning the coordinate system conversion, the purpose of it is to find out the exact position of actual movement of the pupil center. Assume that there are four corners namely the upper left corner (m0,n0), the upper right corner (m1,n1), the lower left corner (m2,n2) and the central point (m3,n3) all shown in the human pupil area image captured by the video capturing device 221. After rotating a certain angle ($\theta$) (which is defined as positive when it rotates counterclockwise), the new coordinate system can be obtained. The new points (m0,n0) and (m0,n0) are just on the horizontal axis of the coordinate system. This angle can be calculated by the following equation.

$$\tan\theta = \frac{n1-n0}{m1-m0}$$

$$\theta = \tan^{-1}\left(\frac{n1-n0}{m1-m0}\right)$$

Figure 8:
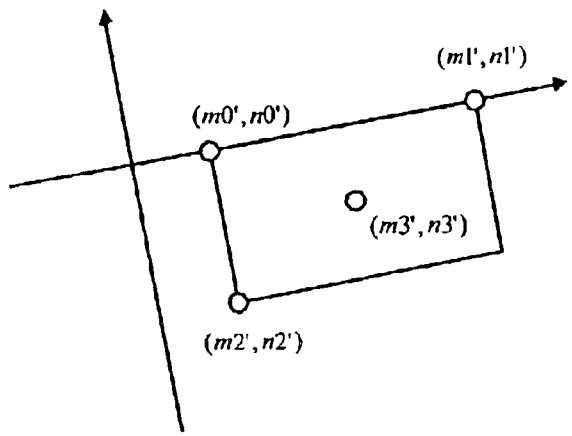
FIG. 8 shows another four reference points after their coordinate system is rotated.

The new coordinate system after rotated can be seen in FIG. 8 and its four reference points (m0,n0), (m1,n1), (m2,n2), and (m3,n3) can be calculated through the following equations.

Figure 9:
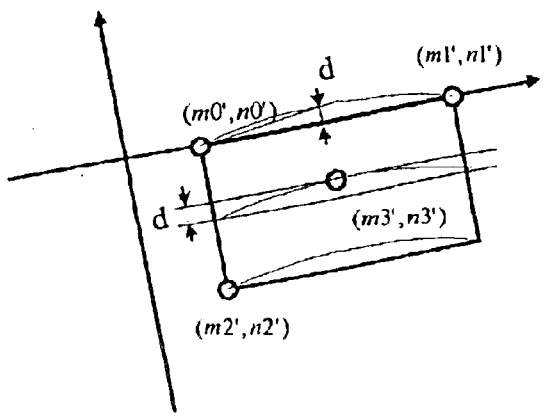
FIG. 9 is a diagram in which the curved moving path of the eye.

$m0'=m0 \cos\theta = n0 \sin\theta$ $n0'=n0 \cos\theta - m0 \sin\theta$ $m1'=m1 \cos\theta = n1 \sin\theta$ $n1'=n1 \cos\theta - m1 \sin\theta$ $m2'=m2 \cos\theta = n2 \sin\theta$ $n2'=n2 \cos\theta - m2 \sin\theta$ $m3'=m3 \cos\theta = n3 \sin\theta$ $n3'=n3 \cos\theta - m3 \sin\theta$ Because the eyeball of a human is spherical, when it rotates horizontally, the pupil center will move along a spherical surface. If an image is captured from a position below with an oblique angle, the moving path of the pupil center will become a curve (not a straight line) as shown in FIG. 9. Suppose that d means the vertical coordinate difference between the central point (m3',n3') and mean value of (m0', n0') and (m2', n2'). This vertical coordinate difference (d) can be obtained by the following equation:

$$d = n3' - \tfrac{1}{2}(n2'-n0')$$

By utilizing interpolation technique within a triangle, the corresponding vertical coordinate difference (d) for any points lying on this curve can be calculated. Assume there is a point at (m,n), if m<m3', then $$d' = \frac{a-m0'}{m3'-m0'}*d$$

If m>m3, then $$d' = \frac{m1'-a}{m1'-m3'}*d$$

Finally, after curved tracking correction, we can obtain correctional coordinates (m', n') as below.

$m'=m$ $n'=n-d'$

By subtracting the vertical coordinate difference d for every point, it can be converted in to a square. Therefore, it will prevent the powered wheelchair to be activated unintentionally due to the error when calculating its pupil center.

If the resolution of the screen of the display device 10 is defined as A*B pixels, by coordinate transformation, the pupil center after converted into the new coordinate system will be:

$$Dm = \frac{A}{(m1'-m0')}*(m'-m0')$$

$$Dn = \frac{B}{(n2'-n0')}*(n'-n0')$$

wherein Dm is the value of the horizontal coordinate, and Dn is the value of the vertical coordinate.

Therefore, when the eyeball moves, an exact point of the pupil center can be obtained more precisely.

Basically, by theses three points, the lower left corner, the upper left corner and the upper right corner, the human pupil area image captured by the video capturing device 221 can be used to ensure the horizontal coordinate and the vertical coordinate so as to calibrate the coordinate system.

In addition, the powered vehicle preferably has a speed. Practically, typical DC (direct current) driving speeder has two kinds, namely the linear speeder and the switching speeder.

FIG. 10A illustrates the circuit diagram of the linear speeder. FIG. 10B shows the input voltage of the linear speeder. FIG. 10C shows its output voltage (Vce) of the transistor. FIG. 10D shows the output of the motor. This kind of speeder utilizes a transistor which works within a linear working zone as a variable resistor to achieve the speed variation. Its advantage includes its simplicity and ease of design. When it works on a full load condition, the loss of the speeder is very small. When it works on a slight load condition, there is almost no loss. When it works on a half-load condition, assuming that the output power is a half of the input power, the impedance of this transistor and the impedance of the motor are equal. So, a half of the power will be consumed by the transistor. Therefore, it is not suitable for the application with larger power consumption.

FIG. 11A is a circuit diagram of the switching speeder.
FIG. 11B shows the input voltage of the switching speeder.
FIG. 11C shows its output voltage (Vce) of the transistor.
FIG. 11D shows the output of the motor. The operation of the transistor falls within the saturation region zone and the cutoff region. Its function is to switch on or off. When it works within the cutoff region, its impedance is quite large. When it works within the saturation region, the impedance is relatively low. Hence, its power conversion efficiency is significantly higher than the one of linear speeder, especially when it works under a larger load condition.

The powered vehicle also needs to have the basic forward and reverse movements. Two types of circuits are commonly used for these forward and reverse movements. One of them is the push-pull circuit operated by a positive and a negative power sources (+Vs, −Vs), as shown in FIG. 12. When the first transistor Q1 is activated, the electricity will pass through the first transistor Q1 and the motor and finally flows to the ground, so that the motor M rotates forward. When the second transistor Q2 is activated, the electricity will pass through the second transistor Q2 and to the negative power source so that the motor rotate reversely. The advantage of the push-pull type is the simplicity of the circuit. Only two transistors are needed to achieve the forward-reverse movements. However, the disadvantage is that both the positive and negative power sources are required. If using a regular rechargeable battery for general powered wheelchair, it only has one power source. Thus, it is not suitable for most powered wheelchair.

Figure 13:
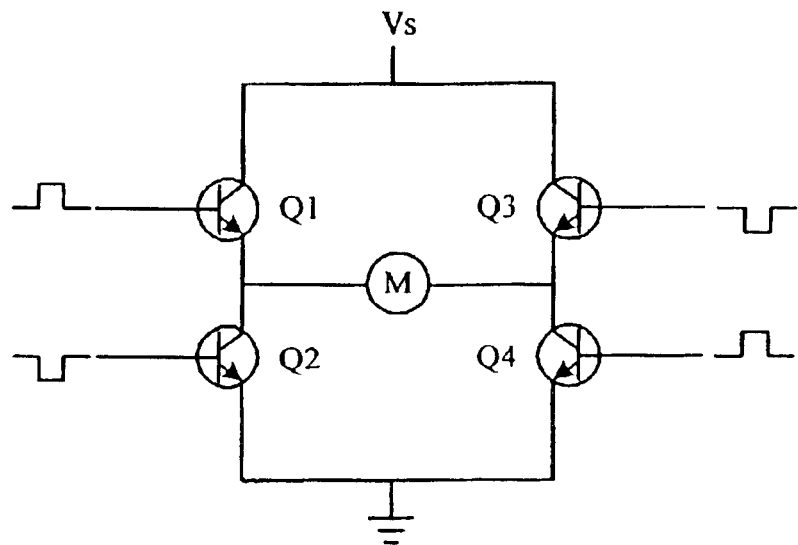
FIG. 13 is a full bridge typed circuit.

The other type is so-called full bridge circuit as shown in FIG. 13. When the first transistor Q1 and the fourth transistor 04 are activated, the electricity will pass through the first transistor Q1, the motor, and the fourth transistor Q4 and then to the ground so that the motor rotates forward. On the contrary, when the second transistor Q2 and the third transistor Q3 are activated, the electricity will pass through the third transistor Q3, the motor, and the second transistor Q2, and then to the ground, so that the motor becomes rotating in a opposite direction (move reverse). The advantage of the full bridge circuit is that only one power source (+Vs) is required to achieve the motor control. But, its disadvantage is that four transistors are needed and the circuit design is more complicated. Thus, the full bridge circuit is more suitable for a general powered wheelchair.

When the user wants to operate this powered vehicle in a tiny space, this user needs to micro adjust the speed or direction. That is, it raises another issue about the command gradient. If there is no such micro-adjustment, the operation command could be too large or too small. Consequently, the powered vehicle cannot be well-controlled. Thus, what we hope is to let the actual command arrives to the motor is smaller than the linear command output, so that it can be well-controlled.

Figure 14:
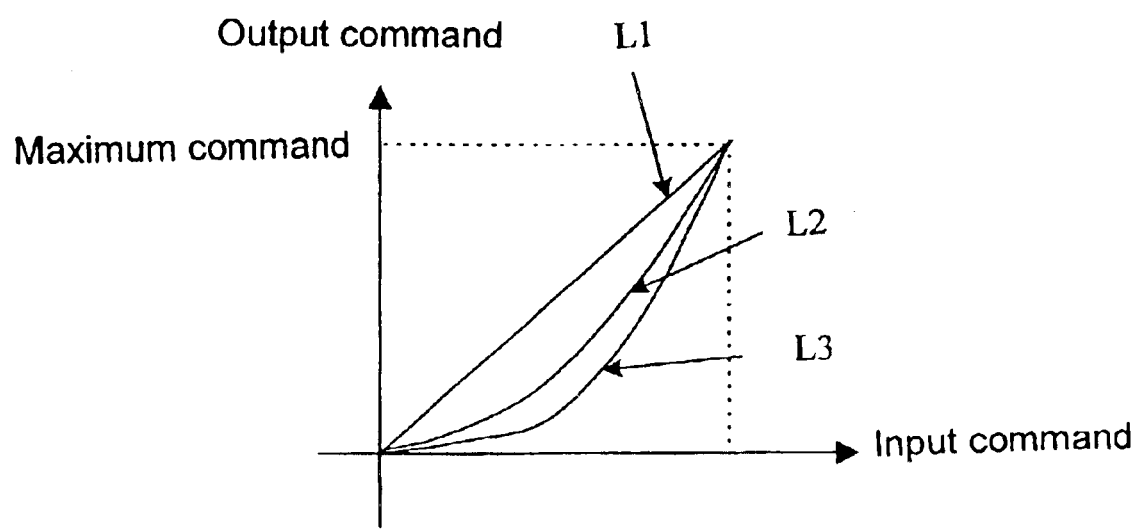
FIG. 14 is a comparison about different command gradients.

FIG. 14 is a comparison about different command gradients. Under the same input command, the output commands the second-order curve L2 and the third-order curve L3 are smaller than the output command of the straight line L1. The maximum output commands of these three curves are the same. Thus, both the second-order curve L2 and the third-order curve L3 are qualified. However, because the imputation for the third-order curve L3 will be more complicated than for the second-order curve L2, the second-order curve L2 is chosen as our final method for gradient command.

Figure 15:
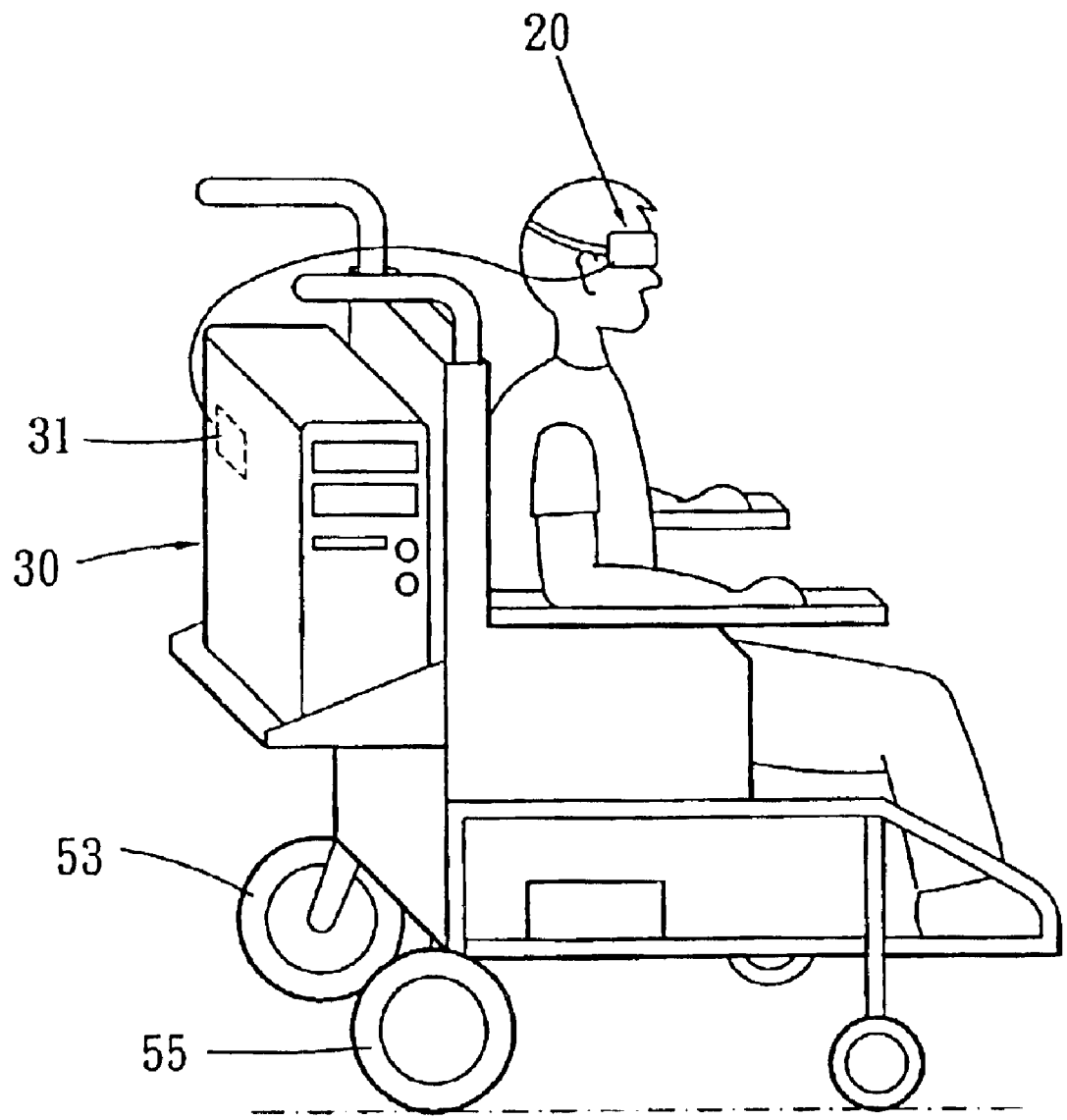
FIG. 15 is a perspective view of the second preferred embodiment of this invention.

Referring to FIG. 15, it is the second preferred embodiment of this invention. In order to eliminate the influence caused by the head's movement for this eye-tracking system, we design a new system by utilizing the top, bottom, leftmost, and rightmost movements of the eye as the operation commands. In this case, the user does not need to look at the screen. All the user needs to do is to move the eye to make a desired operation command.

Figure 16:
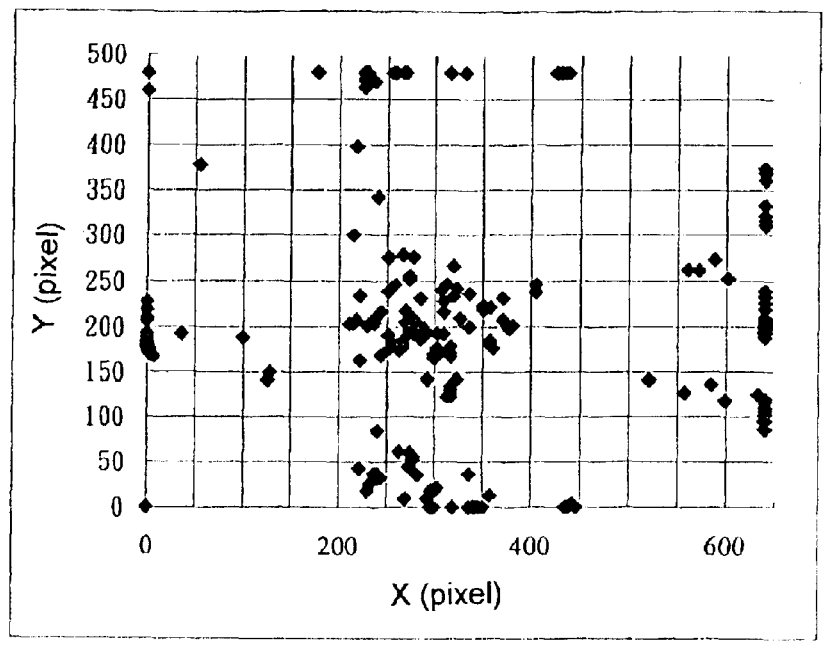
FIG. 16 shows the actual distribution of the pupil centers.

About the detailed structure of the second preferred embodiment, except the display device 10 is omitted, the other portions are identical to the ones in the first preferred embodiment as described above. Also, the user to turn his/her head to look the environment around. FIG. 16 is the actual distribution of the pupil centers. Similarly, it can achieve the same functions as the first preferred embodiment's function.

Figure 17:
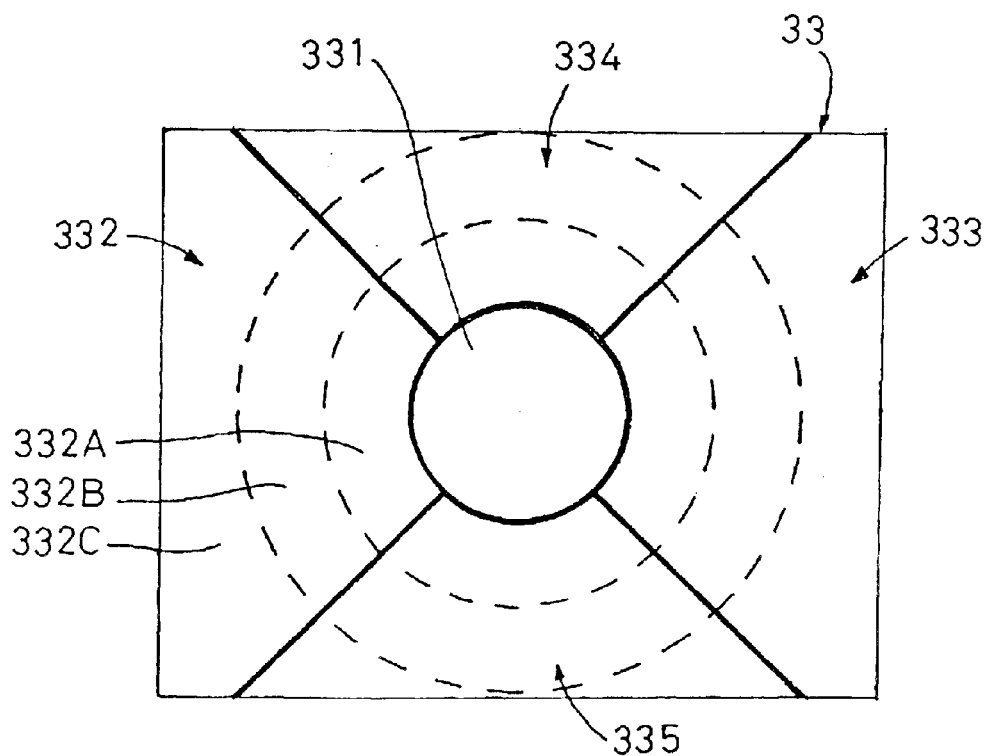
FIG. 17 shows a circular incremental system.

No matter the first or the second preferred embodiments, the calculation device 30 can determine the desired output operation command via the nine zones 32. After the user operates this system for a while (when this user is quite familiar with the operation), the nine zones 32 can be replaced by a circular incremental system as shown in FIG. 17. This circular incremental system 33 includes:

(a) an inner circle zone 331 as the stop command when the pupil center falls in;

(b) an left incremental zone 332 as the left turn command when the pupil center falls in and an output of the left turn command being proportional to a distance between the pupil center and the inner circle zone; For example, it is divided into three sections, namely, the first section 332A, the second section 332B and the third section 332C to represent 1.0, 2.0 and 3.0 units of speed respectively (which means the low speed, medium speed, and high speed). Thus, it will be more convenient for the user to control it.

(c) an right incremental zone 333 as the right turn command when the pupil center falls in and an output of the right turn command being proportional to a distance between the pupil center and the inner circle zone;

(d) an top incremental zone 334 as the forward command when the pupil center falls in and an output of the forward command being proportional to a distance between the pupil center and the inner circle zone; and (e) an bottom incremental zone 335 as the right turn command when the pupil center falls in and an output of the right turn command being proportional to a distance between the pupil center and the inner circle zone.

Of course, each the above incremental zones can be divided into three or more sections for more levels.

The powered vehicle 50 of this invention not only can apply to the powered wheelchair but also to a recreational vehicle or a device of virtual reality game (both can be controlled to move left, right, forward, reverse, and stop or the like). Of course, it can apply to a mini-electrical scooter (or tricycle), mini electrical recreational car or other similar recreational facility.

Above all, this invention utilizes the unique eye-tracking technique to control a powered vehicle or a transportation device. It will not contact the eyes or skin of the user, so it will not injure or discomfort the user. Particularly, it is extremely suitable for disable persons.

The above embodiments are only used to illustrate the present invention, not intended to limit the scope thereof. Many modifications of the above embodiments can be made without departing from the spirit of the present invention.

What is claimed is:

1. An eye-tracking driving system comprising:

a display device disposed in front of a user to look at;

an eye-tracking device having a fixing band portion and a transparent goggles portion, said transparent goggles portion having a video capturing device for obtaining a human pupil area image and an auxiliary light for providing enough brightness of said human pupil area image;

a calculating device to input said human pupil area image via an image capturing interface card and then to calculate a center point of a pupil of said human pupil area image that is defined as a pupil center and to determine staying times and staying positions of said pupil center, and finally to output one of corresponding operation commands, said operation commands at least including: a left turn command, a right turn command, a forward command, a reverse command, and a stop command; wherein said human pupil area image is divided into nine zones substantially consisting by three columns and three rows so as to form a upper left zone, a top zone, a upper right zone, a left zone, a central zone, a right zone, a lower left zone, a bottom zone, and a lower right zone, said central zone, upper left zone, upper right zone, lower left zone, lower right zone are corresponding to said stop command, said left zone, right zone, top zone, and bottom zone are corresponding to said left turn command, right turn command, forward command and reverse command respectively;

a controller to convert said operation command that is an output from said calculating device into a left wheel driving command and a left wheel driving command and a right wheel driving command;

a powered vehicle including a seat, a left driving system, a left wheel, a right driving system, and a right wheel, wherein said left wheel driving system can drive said left wheel according to said left driving command, and said right wheel driving system can drive said right wheel according to said right driving command.

2. The eye-tracking driving system as claimed in claim 1, wherein the left driving system further comprises a left motor, a left gear box and a left clutch; the right driving system further comprises a right motor, a right gear box and a right clutch.

3. The eye-tracking driving system as claimed in claim 1, wherein said video capturing device obtains a lower left corner, an upper left corner, and a upper right corner of said human pupil area image so as to define a horizontal axis and a vertical axis for an coordinate system calibration.

4. The eye-tracking driving system as claimed in claim 1, wherein said vehicle is a recreational vehicle.

5. The eye-tracking driving system as claimed in claim 1, wherein said vehicle is a device of virtual reality game.

6. The eye-tracking driving system as claimed in claim 1, wherein said calculating device being to determine an operation command by means of said nine zones within a predetermined time, after actually operating by a user for a while, said calculating device being to determine an operation command by means of a circular incremental system, said circular incremental system includes:

(a) an inner circle zone as said stop command when said pupil center falls in;

(b) an left incremental zone as said left turn command when said pupil center falls in and an output of said left turn command being proportional to a distance between said pupil center and said inner circle zone;

(c) an right incremental zone as said right turn command when said pupil center falls in and an output of said right turn command being proportional to a distance between said pupil center and said inner circle zone;

(d) an top incremental zone as said forward command when said pupil center falls in and an output of said forward command being proportional to a distance between said pupil center and said inner circle zone; and (e) a bottom incremental zone as said right turn command when said pupil center falls in and an output of said right turn command being proportional to a distance between said pupil center and said inner circle zone.

7. An eye-tracking driving system comprising:

an eye-tracking device having a fixing band portion and a transparent goggles portion, said transparent goggles portion having a video capturing device for obtaining a human pupil area image and a auxiliary light for providing enough brightness of said human pupil area image;

a calculating device to input said human pupil area image via an image capturing interface card and then to calculate a center point of a pupil of said human pupil area image that is defined as a pupil center and to determine staying times and staying positions of said pupil center, and finally to output one of corresponding operation commands, said operation commands at least including: a left turn command, a right turn command, a forward command, a reverse command, and a stop command;

a controller to convert said operation command that is an output from said calculating device into a left wheel driving command and a right wheel driving command; wherein said human pupil area image is divided into nine zones substantially consisting by three columns and three rows so as to form a upper left zone, a top zone, a upper right zone, a left zone, a central zone, a right zone, a lower left zone, a bottom zone, and a lower right zone, said central zone, upper left zone, upper right zone, lower left zone, lower right zone are corresponding to said stop command, said left zone, right zone, top zone, and bottom zone are corresponding to said left turn command, right turn command, forward command and reverse command respectively;

a powered vehicle including a seat, a left driving system, a left wheel, a right driving system, and a right wheel, wherein said left wheel driving system can drive said left wheel according to said left driving command, and said right wheel driving system can drive said right wheel according to said right driving command.

8. The eye-tracking driving system as claimed in claim 7, wherein said left driving system further comprises a left motor, a left gear box and a left clutch; said right driving system further comprises a right motor, a right gear box and a right clutch.

9. The eye-tracking driving system as claimed in claim 7, wherein said vehicle is a recreational vehicle.

10. The eye-tracking driving system as claimed in claim 7, wherein said vehicle is a device of virtual reality game.

11. The eye-tracking driving system as claimed in claim 7, wherein said calculating device being to determine an operation command by means of said nine zones within a predetermined time, after actually operating by a user for a while, said calculating device being to determine an operation command by means of a circular incremental system, said circular incremental system includes:

(a) an inner circle zone as said stop command when said pupil center falls in;

(b) an left incremental zone as said left turn command when said pupil center falls in and an output of said left turn command being proportional to a distance between said pupil center and said inner circle zone;

(c) an right incremental zone as said right turn command when said pupil center falls in and an output of said right turn command being proportional to a distance between said pupil center and said inner circle zone;

(d) an top incremental zone as said forward command when said pupil center falls in and an output of said forward command being proportional to a distance between said pupil center and said inner circle zone; and (e) a bottom incremental zone as said right turn command when said pupil center falls in and an output of said right turn command being proportional to a distance between said pupil center and said inner circle zone.

* * * * *